United States Patent [19]
Sakai et al.

[11] Patent Number: 5,508,391
[45] Date of Patent: Apr. 16, 1996

[54] CRYSTALLINE 2-O-α-D-GLUCOPYRANOSYL-L-ASCORBIC ACID, AND ITS PREPARATION AND USES

[75] Inventors: Shuzo Sakai; Masaru Yoneyama; Toshio Miyake, all of Okayama, Japan

[73] Assignee: Kabushiki Kaisha Hayashibara, Okayama, Japan

[21] Appl. No.: 358,400

[22] Filed: Dec. 19, 1994

Related U.S. Application Data

[63] Continuation of Ser. No. 501,900, Mar. 30, 1990, Pat. No. 5,432,161.

[30] Foreign Application Priority Data

Oct. 21, 1989 [JP] Japan .................................. 1-274019

[51] Int. Cl.$^6$ ............................................ G07H 17/04
[52] U.S. Cl. ........................ 536/4.1; 536/1.11; 536/120; 549/315
[58] Field of Search ........................... 536/1.11, 4.1, 536/120; 549/315; 514/23, 25, 27

[56] References Cited

U.S. PATENT DOCUMENTS

| | | | |
|---|---|---|---|
| 1,235,198 | 7/1917 | Gams et al. | 514/474 |
| 3,012,942 | 12/1961 | Morse | 514/474 |
| 3,669,835 | 6/1972 | Suzuki | 435/66 |
| 3,763,009 | 10/1973 | Suzuki et al. | 536/18.2 |
| 4,254,227 | 3/1981 | Okada et al. | 435/193 |
| 4,533,674 | 8/1985 | Schmidt et al. | 514/474 |
| 4,629,567 | 12/1986 | Bollen et al. | 534/815 |
| 4,753,881 | 6/1988 | Yeh et al. | 435/815 |
| 4,758,349 | 7/1988 | Ma | 435/815 |
| 5,084,563 | 1/1992 | Sakai et al. | 536/18.5 |
| 5,137,723 | 8/1992 | Yamamoto et al. | 536/18.6 |
| 5,272,136 | 12/1993 | Mandai et al. | 514/27 |
| 5,338,420 | 8/1994 | Aga et al. | 204/182.6 |
| 5,407,812 | 4/1995 | Sakai et al. | 536/4.1 |
| 5,432,161 | 7/1995 | Sakai et al. | 514/23 |

FOREIGN PATENT DOCUMENTS 4838158  9/1972  Japan .

*Primary Examiner*—Michael G. Wityshyn
*Assistant Examiner*—Everett White
*Attorney, Agent, or Firm*—Browdy and Neimark

[57] ABSTRACT

2-O-α-D-Glucopyranosyl-L-ascrobic acid is crystallizable in its supersaturated solution. Crystalline 2-O-α-D-glucopyranosyl-L-ascorbic acid is substantially nonhygroscopic, free flowing, free of deliquescence, consolidation and direct reducing activity, but is readily soluble in water. Because of these characteristics, crystalline 2-O-α-D-glucopyranosyl-L-ascorbic acid is handleable with an ease, and superiorly high in stability and physiological activities. Thus, crystalline 2-O-α-D-glucopyranosyl-L-acorbic acid is favorably useful in vitamin C-enriching agents, foodstuffs, pharmaceuticals and cosmetics.

2 Claims, 5 Drawing Sheets

CRYSTALLINE 2-O-α-D-GLUCOPYRANOSYL-L-ASCORBIC ACID, AND ITS PREPARATION AND USES

This is a continuation of parent application Ser. No. 07/501,900, filed Mar. 30, 1990 now U.S. Pat. No. 5,432,161.

BACKGROUND OF THE INVENTION

1. Field of the Invention

The present invention relates to a novel substance, a crystalline 2-O-α-D-glucopyranosyl-L-ascorbic acid, and its preparation and uses.

2. Description of the Prior Art

L-Ascorbic acid, which has the chemical structure shown by the formula [I]:

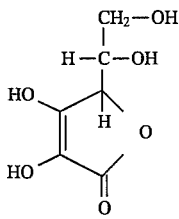

is not synthesized in vivo in human, monkey and guinea pig, and therefore is listed as an essential nutritive element, i.e. vitamin C.

L-Ascorbic acid takes part in some physiological activities in vivo; for example, in the hydroxylation of proline and lysine which are necessary to synthesize collagen as the main element of living connective tissues; the oxidation-reduction reaction of cytochrome C wherein $Fe^{+++}$ is reduced into $Fe^{++}$; and in immunopotentiation via the increase of leukocytes. Thus vitamin C plays a significant role in the maintenance and promotion of health in living body.

Scurvy has been known long as a condition due to a deficiency of L-ascorbic acid, and is marked by weakness of the skin, petechial hemorrhage, ecchymosis, and hemorrhages in the gingiva and marrow. To prevent scurvy for the maintenance of health, a recommended daily administration (RDA) is established for L-ascorbic acid; in particular, 60 mg for adult males and 50 mg for adult females.

Nowadays the use of L-ascorbic acid is not limited to agents which enrich vitamin C as an essential nutritive element, but is extending to various applications. More particularly, because of its chemical structure and physiological activities, L-ascorbic acid is useful as a souring agent, reductant, antioxidant, bleaching agent and stabilizer in various chemical reagents, foods and beverages; in pharmaceuticals against susceptive diseases such as prevention and treatment for viral diseases, bacterial diseases and malignant tumors; and further as a reductant, uv-absorbent and melanin-formation inhibitor in cosmetics including skin-refining agent and skin-whitening agent.

The major drawback of L-ascorbic acid is that it readily loses its physiological activities because of its direct reducing activity, poor stability and high susceptibility to oxidation.

To stabilize L-ascorbic acid, some saccharide derivatives of L-ascorbic acid have been proposed. For example, we disclosed in Vitamin, Vol.43, pp.205–209 (1971), ibid., Vol.47, pp.259–267 (1973), and Japanese Patent Publication No.38,158/73 a biochemical synthesis of L-ascorbic acid glucosides.

Because of the facts that the glucosides are prepared by similar methods; that the formation of an ether bond at the primary alcohol group which is located at the number six carbon atom in L-ascorbic acid leads to the glucosides as described in the Japanese Patent Publication, for example, on the 2nd column, lines 14–16; that the saccharide-transfer reaction from maltose to an α-glucosyl group is responsible for the formation of glucosides; and that the glucosides exhibit a direct reducing activity, their chemical structure would be shown by the formula [II]:

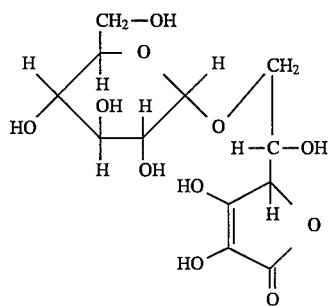

As obvious from the results in the Japanese Patent Publication, the table in Example 1, the stability of the glucosides is superior to that of L-ascorbic acid, but is not enough for their commercialization.

Ishido et al. disclose in Japanese Patent Publication No.5,920/83 an organic chemical process to synthesize saccharide derivatives of L-ascorbic acid.

These derivatives are, however, those wherein all the D-glucoses are bound in the β-fashion because up to 21 β-D-glucopyranosyl type derivatives of L-ascorbic acid including 2,3-di-O-(β-D-glucopyranosyl)-L-ascorbic acid are listed for explanation on the 7th column, line 6 to the 8th column, line 11.

Masamoto et al. disclose in Japanese Patent Publication No.198,498/83 an organic chemical process to synthesize saccharide derivatives of L-ascorbic acid which are also of the β-glucosyl type.

Studies on the β-D-glucopyranosyl type derivatives of L-ascorbic acid confirmed that they hardly exhibit desired physiological activities in living body, especially in humans. Furthermore, conventional organic chemical processes have the drawbacks that they are inferior in economical efficiency because the reaction is very complicated and low in yield, and the establishment of non-toxicity and safeness for the resultant derivatives is very difficult.

As described above, the proposals of saccharide derivatives of L-ascorbic acid in the prior art have proved unsatisfactory in view of stability, safeness, physiological activity and economical efficiency, and not been practiced hitherto.

The present invention has as an object to overcome the drawbacks of conventional saccharide derivatives of L-ascorbic acid. More particularly, we studied a novel saccharide derivative of L-ascorbic acid which is obtainable by a biochemical process utilizing a saccharide-transfer reaction.

As disclosed in the specification of Japanese Patent Application No.127,072/89, we discovered a novel substance, an α-glycosyl-L-ascorbic acid, especially, 2-O-α-D-glucopyranosyl-L-ascorbic acid, which is free from direct reducing activity, superiorly stable, readily hydrolyzable in vivo, and satisfactorily high in physiological activity, as well as developing its preparation and uses in foods, beverages, pharmaceuticals for susceptive diseases, and cosmetics.

It was also found that since, when L-ascorbic acid is ingested with an α-glucosyl saccharide, 2-O-α-D-glucopyranosyl-L-ascorbic acid is synthesized and then metabolized in vivo, it would be an ideally convenient, novel saccharide derivative of L-ascorbic acid in view of its safety.

A powder which is obtainable by concentrating and pulverizing an aqueous solution of 2-O-α-D-glucopyranosyl-L-ascorbic acid is amorphous and strongly hygroscopic, and has the drawback that it readily absorbs moisture under ambient conditions to cause deliquescence and consolidation.

SUMMARY OF THE INVENTION

Accordingly, another object of the present invention is to overcome the drawback of such an amorphous 2-O-α-D-glucopyranosyl-L-ascorbic acid, in particular, to provide a satisfactorily free flowing powder which is free from substantial hygroscopicity and consolidation under ambient conditions.

We studied 2-O-α-D-glucopyranosyl-L-ascorbic acid solids which exhibit a substantial nonhygroscopicity under ambient conditions which is enough to overcome the drawback of amorphous 2-O-α-D-glucopyranosyl-L-ascorbic acid.

As the result, we discovered a novel substance, a crystalline 2-O-α-D-glucopyranosyl-L-ascorbic acid, as well as finding that it provides a substantially nonhygroscopic, satisfactorily free flowing, anhydrous crystalline powder which causes neither deliquescence nor consolidation under ambient conditions. Further, we developed a process to prepare such a crystalline 2-O-α-D-glucopyranosyl-L-ascorbic acid, and also processes to prepare foodstuffs, pharmaceuticals for susceptive diseases and cosmetics which all contain the same.

DETAILED DESCRIPTION OF THE INVENTION

Figure 1:
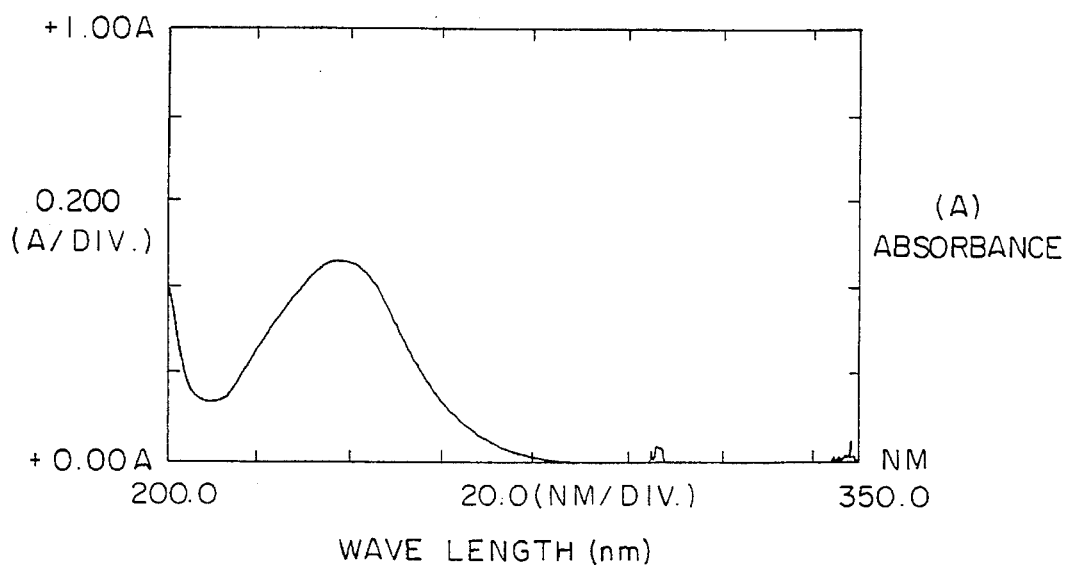
FIG. 1 is the uv-absorption spectrum of a crystalline 2-O-α-D-glucopyranosyl-L-ascorbic acid according to the invention when in a solution at pH 2.0.

The present invention is feasible with any 2-O-α-D-glucopyranosyl-L-ascorbic acid, regardless of its preparation process such as biochemical and organic chemical processes.

In view of safety and economical efficiency, 2-O-α-D-glucopyranosyl-L-ascorbic acid is desirably formed by a biochemical process wherein a saccharide-transferring enzyme is allowed to act alone or together with glucoamylase on a solution containing L-ascorbic acid and an α-glucosyl saccharide.

The wording "exhibiting no direct reducing activity" means that unlike L-ascorbic acid, a saccharide derivative thereof does not reduce and decolor 2,6-dichlorophenolindophenol intact.

The wording "L-ascorbic acid" as referred to in the present invention means L-ascorbates such as alkaline metal salts, alkaline earth metal salts and mixtures thereof, and should not be restricted to free L-ascorbic acid, as far as the present invention is feasible therewith. Thus, if necessary, such as sodium L-ascorbate and calcium L-ascorbate are suitably usable in the saccharide-transfer reaction, as well as free L-ascorbic acid.

The wordings "α-glycosyl-L-ascorbic acid" and "2-O-α-D-glucopyranosyl-L-ascorbic acid" mean, in addition to those in free acid form, as far as the present invention is feasible therewith.

The α-glucosyl saccharides usable in the invention are those which permit a saccharide-transferring enzyme to form from L-ascorbic acid an α-glycosyl-L-ascorbic acid wherein equimolar or more α-D-glucosyl residues are bound to L-ascorbic acid. For example, maltooligosaccharides such as maltose, maltotriose., maltoteraose, maltopentaose, maltohexaose, maltoheptaose and maltooctaose are suitably chosen, as well as partial starch hydrolysates such as dextrin, cyclodextrin and amylose, liquefied starch, gelatinized starch, and solubilized starch.

Consequently to facilitate the formation of α-glycosyl-L-ascorbic acid, one should choose an α-glucosyl saccharide which is susceptible to the saccharide-transferring enzyme to be used.

For example, when α-glucosidase (EC 3.2.1.20) is used as the saccharide-transferring enzyme, maltooligosaccharides such as maltose, maltotriose, maltotetraose, maltopentaose, maltohexaose, maltoheptaose and maltooctaose are suitable, as well as partial starch hydrolysates and dextrins with a DE (Dextrose Equivalent) of about 5–60. When cyclomaltodextrin glucanotransferase (EC 2.4.1.19) is used as the saccharide-transferring enzyme, partial starch hydrolysates such as gelatinized starches with a DE below 1 and dextrins with a DE up to 60 are suitable. When α-amylase (EC 3.2.1.1) is used as the saccharide-transferring enzyme, partial starch hydrolysates such as gelatinized starch with a DE below 1 and dextrins with a DE up to about 30 are suitable.

The concentration of L-ascorbic acid during the reaction is generally 1 w/v % or higher, preferably, about 2–30 w/v %, while the concentration of an α-glucosyl saccharide is generally about 0.5- to 30-fold higher than that of L-ascorbic acid.

The saccharide-transferring enzymes usable in the invention are those which transfer one or several α-glucosyl groups at least to the number two carbon atom in L-ascorbic acid without decomposing it when allowed to act on a solution which contains L-ascorbic acid and an α-glucosyl saccharide having an adequate susceptivity to the enzyme.

For example, α-glucosidases derived from animals, plants and microorganisms such as those from mouse kidney, rat intestinal mucosa, dog small intestine, pig small intestine, rice seed, maize seed, and those from a culture which is obtainable by cultivating in a nutrient culture medium yeasts and bacteria of the genera Mucor, Penicillium and Saccharomyces; cyclomaltodextrin glucanotransferases from a culture of bacteria such as those of the genera Bacillus and Klebsiella; and α-amylase from a culture of bacteria such as those of the genus Bacillus are suitably chosen.

Such a saccharide-transferring enzyme need not necessarily be purified prior to its use, as long as it fulfills the above requirements. Generally, the present invention is feasible with a crude enzyme. If necessary, saccharide-transferring enzymes can be purified by conventional method, prior to its use. Of course, commercialized saccharide-transferring enzymes can be used in the invention. The amount of a saccharide-transferring enzyme and reaction time are closely dependent upon each other. With an economical viewpoint, saccharide-transferring enzyme is used in an amount which completes the reaction within about 3–80 hours.

Immobilized saccharide-transferring enzymes are favorably usable batchwise and in continuous manner.

The reaction process according to the invention is usually carried out by adding a saccharide-transferring enzyme to a solution containing the above described L-ascorbic acid and an α-glucosyl saccharide, and keeping the mixture under conditions where the enzyme is substantially active; usually, at a pH in the range of about 3–9 and a temperature in the range of about 20°–80° C. Since during the reaction, L-ascorbic acid tends to cause an oxidative decomposition, it is desirable to keep the mixture under conditions which shield aeration and light as far as possible so that L-ascorbic acid is in its reducing form. The reaction is favorably carried out in the presence of such as thiourea and hydrogen sulfide, if necessary.

The desired substance can be obtained by incorporating L-ascorbic acid and an α-glucosyl saccharide in the culture of a growing microorganism which is capable of producing a saccharide-transferring enzyme.

Generally, the reaction process according to the invention is carried out by allowing a saccharide-transferring enzyme to act alone or together with glucoamylase on a solution which contains L-ascorbic acid and an α-glucosyl saccharide.

Such a process is feasible with glucoamylases derived from various sources such as microorganisms and plants. Usually, commercialized glucoamylase derived from a microorganism of the genera Aspergillus and Rhizopus are suitable.

To form 2-O-α-D-glucopyranosyl-L-ascorbic acid, glucoamylase can be used simultaneously with a saccharide-transferring enzyme. Generally to improve the reaction efficiency, desirably, a saccharide-transferring enzyme is first used to transfer equimolar or more D-glucose residues to L-ascorbic acid to form an α-glycosyl-L-ascorbic acid, then glucoamylase is used to accumulate 2-O-α-D-glucopyranosyl-L-ascorbic acid. β-Amylase (EC 3.2.1.2) can be freely used along with glucoamylase.

Alpha-glycosyl-L-ascorbic acids formed by such a saccharide-transferring enzyme bear an α-D-glucosyl group consisting of 1–7 glucosyl groups linked via the α-1,4 fashion, and such an α-D-glucosyl group is bound at least to the primary alcohol group which is located at the number two carbon atom. Particular substances are, for example, 2-O-α-D-glucosyl-L-ascorbic acid, 2-O-α-D-maltosyl-L-ascorbic acid, 2-O-α-maltotriosyl-L-ascorbic acid, 2-O-α-D-maltotetraosyl-L-ascorbic acid, 2-O-α-D-maltopentaosyl-L-ascorbic acid, 2-O-α-D-maltohexaosyl-L-ascorbic acid and 2-O-α-D-maltoheptaosyl-L-ascorbic acid. Although α-glucosidase generally forms only 2-O-α-D-glucosyl-L-ascorbic acid, 2-O-α-D-maltosyl-L-ascorbic acid and 2-O-α-D-maltotriosyl-L-ascorbic acid can be formed in mixture, if necessary.

In the case of using either cyclomaltodextrin glucanotransferase or α-amylase, α-glycosyl-L-ascorbic acids with a higher α-D-glucosyl group are formed in mixture. Dependently on the α-glucosyl saccharide, cyclomaltodextrin glucanotransferase yields an α-D-glucosyl group with a polymerization degree distributing in the range of 1–7, while α-amylase yields a slight narrower distribution. Such a mixture can be partially hydrolyzed with either of α-amylase (EC 3.2.1.1), β-amylase (EC 3.2.1.2) and glucoamylase (EC 3.2.1.3 ) to reduce the polymerization degree of the α-D-glucosyl group, if necessary. For example, 2-O-α-D-maltosyl-L-ascorbic acid and higher polymers are hydrolyzed to accumulate 2-O-α-D-glucosyl-L-ascorbic acid when subjected to glucoamylase. β-Amylase predominantly hydrolyzes 2-O-α-D-maltotetraosyl-L-ascorbic acid and higher polymers to accumulate 2-O-α-D-glucosyl-L-ascorbic acid, 2-O-α-D-maltosyl-L-ascorbic acid and 2-O-α-D-maltotriosyl-L-ascorbic acid in mixture.

Reaction mixtures obtained by these methods usually contains the remaining L-ascorbic acid, D-glucose and α-glucosyl saccharide together with 2-O-α-D-glucopyranosyl-L-ascorbic acid.

When needed as a refined product with a high 2-O-α-D-glucopyranosyl-L-ascorbic acid content, such a reaction mixture is subjected to one or more separations methods wherein the difference between 2-O-α-D-glucopyranosyl-L-ascorbic acid and contaminants such as remaining L-ascorbic acid, D-glucose and α-glucosyl saccharides in molecular weight and/or affinity is utilized; for example, membrane separation, gel filtration chromatography, column chromatography, high-performance liquid chromatography (HPLC) and ion exchange chromatography. In this case, the separated L-ascorbic acid and α-glucosyl saccharide can be favorably reused as a starting material in the saccharide-transfer reaction. If necessary, after completion of the saccharide-transfer reaction but before separation such as by chromatography, the reaction mixture can be treated by one or more methods; for example, a method wherein the reaction mixture is heated and the insolubilized substances are removed by filtration; another method wherein the reaction mixture is treated, for example, with activated carbon to adsorb the proteinaceous and coloring substances for their removal; and another method wherein the reaction mixture is demineralized with cation exchange resin ($H^+$-form), and treated with anion exchange resin ($OH^-$-form) to remove anions and salts by adsorption.

The following will explain the crystallization of 2-O-α-D-glucopyranosyl-L-ascorbic acid. Crystallizable 2-O-α-D-glucopyranosyl-ascorbic acid is usually in the form of a supersaturated solution, and any 2-O-α-D-glucopyranosyl-L-ascorbic acid specimen can be used regardless of its preparation process, as far as a crystalline 2-O-α-D-glucopyranosyl-L-ascorbic acid is obtainable therefrom. The degree of supersaturation is usually set to about 1.05–1.5. More particularly, 2-O-α-D-glucopyranosyl-L-ascorbic acid, purity of about 75% or higher, is prepared into an about 65–95 w/w % aqueous solution, and the temperature is set to a level which does not freeze the solution and causes a less heat loss during the processing, desirably, in the range of 0°–95° C. The degree of supersaturation and viscosity are controllable by the addition of such as methanol, ethanol and acetone. A supersaturated solution of 2-O-α-D-glucopyranosyl-L-ascorbic acid is placed at a relatively high temperature such as 20°–60° C. in a crystallizer, added with a seed crystal, desirably, in an amount of 0.1–10 w/w %, and crystallized into massecuite while accelerating the crystallization by gentle stirring. In this way, the crystalline 2-O-α-D-glucopyranosyl-L-ascorbic acid of the invention is easily obtainable by seeding a supersaturated solution of 2-O-

α-D-glucopyranosyl-L-ascorbic acid. To prepare the resultant massecuite into final crystalline product, conventional methods, for example, separation, block-pulverization, spray-drying and fluidized-bed granulation methods are employable.

The separation method, wherein a massecuite is usually separated into crystalline 2-O-α-D-glucopyranosyl-L-ascorbic acid and mother liquor (molasses) with a basket-type centrifuge, is convenient in the preparation of a nonhygroscopic high-purity crystalline 2-O-α-D-glucopyranosyl-L-ascorbic acid, and the separated crystal can be washed by spraying thereto a small amount of water when a much higher purity is needed. The separated mother liquor is purified and concentrated similarly as above into a massecuite which is then reused to recover such as second and third crystalline crops. This improves the yield of crystalline 2-O-α-D-glucopyranosyl-L-ascorbic acid.

Since the other three methods do not remove molasses, they never improve the purity of crystalline 2-O-α-D-glucopyranosyl-L-ascorbic acid in final powdery products, but realize a high product yield. Accordingly, such a product usually contains, for example, L-ascorbic acid, 2-O-α-D-maltosyl-L-ascorbic acid, higher α-glycosyl-L-ascorbic acids, glucose and α-glucosyl saccharides along with crystalline 2-O-α-D-glucopyranosyl-L-ascorbic acid.

In the case of spray-drying, usually, a massecuite with both concentration of 70–85 w/w % and crystallinity of 25–60 w/w % is spray-dried through a high-pressure nozzle, and the obtained droplets are dried in an air stream of a temperature, for example, 30°–60° C., which does not melt crystalline powder, and then aged in a stream of 30°–60° C. air for about 1–20 hours. Thus, a nonhygroscopic or scarcely hygroscopic crystalline powder is obtainable with an ease. In the case of block-pulverization, usually, a massecuite with both moisture content of 5–15 w/w % and crystallinity of about 10–60 w/w % is allowed to stand for 0.5–5 days so that the whole content is crystallized and solidified into block. Cutting and drying of the resultant block readily yield a nonhygroscopic or scarcely hygroscopic crystalline powder.

Alternatively, 2-O-α-D-glucopyranosyl-L-ascorbic acid in solution is concentrated by heating into a supersaturated solution in melting form, moisture content below 5 w/w %, which is then kneaded along with a 2-O-α-D-glucopyranosyl-L-ascorbic acid seed crystal at a temperature below its melting point, and prepared into a desired form, for example, powder, granule, rod, plate and cube. Thus, a nonhygroscopic or scarcely hygroscopic crystalline solid is obtainable. Dependent on both purity and crystallinity, the crystalline 2-O-α-D-glucopyranosyl-L-ascorbic acid obtained in this way is substantially nonhygroscopic or scarcely hygroscopic, free flowing, and free of adhesion. Some of its advantages are as listed below:

(1) It exhibits no direct reducing activity, and is extremely stable. Unlike L-ascorbic acid, it scarcely causes the Maillard reaction. Because of these characteristics, it effects no undesired reaction when mixed with such as protein, lipid, saccharide and physiologically-active substance, but stabilizes these substances.

(2) It is susceptible to hydrolysis to form L-ascorbic acid, and this elicits the same reductant and antioxidant activities as L-ascorbic acid.

(3) It is readily hydrolyzable by the in vivo enzyme system into D-glucose and L-ascorbic acid, and thus the physiological activities inherent to L-ascorbic acid are elicited.

(4) It is highly safe because it is synthesized and then metabolized in vivo when L-ascorbic acid is ingested together with an α-glucosyl saccharide.

(5) It is substantially nonhygroscopic or scarcely hygroscopic, but exhibits a high dissolution rate or solubility in water. Because of these characteristics, it is favorably usable as a vitamin C-enriching agent, taste-improving agent, souring agent and stabilizer in foods and beverages, in powder, granule and tablet, such as vitamin compound, cream filling, chocolate, chewing gum, instant juice and seasoning mix.

(6) It is substantially nonhygroscopic or scarcely hygroscopic, free flowing, and free from consolidation. Thus, it is much more easily handled than amorphous product, and this considerably cuts the material and labor costs in packaging, transportation and storage.

Because of these advantages, crystalline 2-O-α-D-glucopyranosyl-L-ascorbic acid can be favorably incorporated as a stabilizer, taste-improving agent, souring agent, antioxidant, quality-improving agent, uv-absorbent, and preventive and remedy for susceptive diseases including viral diseases, bacterial diseases, circulatory diseases and malignant tumors, desirably in an amount of 0.001 w/w % or more, along or in combination with one or more ingredients in foods, beverages, feeds, pet foods, pharmaceuticals for susceptive diseases, and cosmetics such as skin-refining agents and skin-whitening agents, as well as in agents directed to enrich a highly-safe, natural vitamin C. In this case, L-ascorbic acid, vitamin E, rutin, α-glycosyl rutin and/or hesperidin are favorably usable in combination with crystalline 2-O-α-D-glucopyranosyl-L-ascorbic acid.

Since crystalline 2-O-α-D-glucopyranosyl-L-ascorbic acid is highly resistant to acid and heat, and well harmonizes with various substances which taste sour, salty, bitter, delicious and astringent, it is favorably usable as a vitamin C-enriching agent, taste-improving agent, antioxidant and quality-improving agent in foods and beverages in general, for example, seasonings such as soy sauce, say sauce powder, miso, miso powder, "morom", "hishio", "furikake", mayonnaise, dressing, vinegar, "sanbai-zu", "funmatsu-sushi-su", "chuka-nomoto", "tentsuyu (soup for tenpura)", "mentsuyu (soup for Japanese-style noodles)", Worcester sauce, ketchup, "yakinikuno-tare (soup for grilled meat)", curry roux, stew premix, soup premix, "dashi-no-moto", mixed seasoning, "mirin (heavily sweetened sake)", "shin-mirin (synthetic mirin)", table sugar and coffee sugar; Japanese-style confectioneries such as "senbei (rice crackers)", "arare (pellet-shaped senbei)", "okoshi (millet-and rice cracker )", "karinto (fried dough cookie)", "gyuhi (starch paste)", rice paste, "manju (bun with a bean-jam filling)", "uiro (sweet rice jelly)", "an (bean jam)", "yokan (sweet jelly of beans)", "mizu-yokan (soft adzuki-bean jelly)", "kingyoku", jelly castella and "amedama (Japanese-style toffee)"; Western-style confectioneries such as bun, biscuit, cracker, cookie, pie, pudding, cream puff, waffle, sponge cake, doughnut, chocolate, chewing gum, caramel and candy; frozen desserts such as ice cream and sherbet; syrups such as those for fruit preserve and "kaki-gori (shaved ice)"; spreads and pastes such as butter cream, custard cream, flour paste and fruit paste; processed fruits such as jam, marmalade, syrup-preserved fruit and crystallized fruit; processed foods such as those of fruits and vegetables; cereals such as bakery product, noodle, vermicelli, boiled rice and synthetic meat; fatty food substances such as salad oil and margarine; pickled products such as "fukujin-zuke (sliced vegetables picked in soy sauce)", "bettara-zuke (fresh radish pickles)", "senmai-zuke" and "rakkyo-zuke (pickled shallots)"; premixes for pickled products such as "takuan-zuke-no-moto" and "hakusai-zuke-no-moto"; meat products such as ham and sausage; fish meat products such as fish meat ham, fish meant sausage, "kamaboko (boiled fish paste)", "chikuwa (literally bamboo wheels)" and "hanpen"; relishes such as "uni-no-shiokara (salted guts of sea urchin)", "ika-no-shiokara (salted guts of squid)", "su-konbu", "saki-surume" and "fugu-no-mirinboshi"; "tsukudani (food boiled down in soy sauce)" such as those of "nori (dried seaweed)", "sansai (mountain vegetables)", "surume (dried squid)", small fish and shellfish; daily dishes such as "nimame (cooked beans)", potato salad, "konbu-maki (tangle roll)" and "tenpura (deep-fried foods)"; egg and milk products such as "kinshi-tamago", milk beverage, butter and cheese; bottled and canned products such as those of meat, fish meat, fruit and vegetable; alcoholic drinks such as synthetic sake, "zojo-shu", liqueur, wine and whisky; beverages such as coffee, cocoa, juice, carbonated beverage, lactic acid beverage and lactobacillus beverage; and premieres and instant foodstuffs such as pudding premix, hot cake premix, instant juice, instant coffee, "sokuseki-shiruko (premix of adzuki-bean soup with rice cake)" and instant soup. Furthermore, crystalline 2-O-α-D-glucopyranosyl-L-ascorbic acid can be favorably incorporated in feeds and pet foods for domestic animals and poultries including honey bee, silkworm and pet fish for the enrichment of vitamin C, the improvement of their taste qualities and the prevention of oxidation.

Also 2-O-α-D-glucopyranosyl-L-ascorbic acid can be favorably incorporated in special foods and beverages, preventives and remedies for susceptive diseases, cosmetics including skin-refining agent and skin-whitening agent, for example, cigar, cigarette, troche, cod-liver oil drop, vitamin compound, oral refreshing agent, cachou, gargle, intubation nutrient, internal medicine, injection, dentifrice, lipstick, eye shadow, milky lotion, moisture liquid, cosmetic cream, foundation, sunscreen agent, cleansing soap, shampoo and rinse, in addition to the uses as uv-absorbent and deterioration-preventing agent for plastics and also as a substrate for assaying glycoside hydrolases.

The wording "susceptive diseases" as referred to in the invention means those which are prevented and/or treated with crystalline 2-O-α-D-glucopyranosyl-L-ascorbic acid and its solution; for example, viral diseases, bacterial diseases, traumatic diseases, immunopathies, allergy, diabetes, cataract, circulatory diseases and malignant tumors. The shape and form of pharmaceuticals for susceptive diseases can be freely chosen to meet to their final use; for example, liquid pharmaceuticals such as nebula, collyrium, coltunarium, collutory and injection, paste pharmaceuticals such as ointment, cataplasm and cream, and solid pharmaceuticals such as powder, granule, capsule and tablet. In the preparation of such a pharmaceutical, one or more ingredients, for example, remedy, biologically-active substance, antibiotic, adjuvant, filler, stabilizer, coloring agent and flavoring agent, can be suitably used in combination, if necessary.

The dose is adequately changed dependently on the 2-O-α-D-glucopyranosyl-L-ascorbic acid content, administration route and administration frequency; usually, in the range of about 0.001–100 g/day/adult as 2-O-α-D-glucopyranosyl-L-ascorbic acid.

Cosmetics can be prepared similarly as in pharmaceuticals.

Crystalline 2-O-α-D-glucopyranosyl-L-ascorbic acid is incorporated in products by conventional method, for example, mixing, kneading, dissolving, melting, soaking, permeating, spreading, applying, coating, spraying, injecting, crystallizing and solidifying, before completion of their processing.

Crystalline 2-O-α-D-glucopyranosyl-L-ascorbic acid is favorably usable as a material for chemical reactions which are effected under anhydrous conditions because it is substantially anhydrous, and its complete anhydrousness is attainable by a brief ventilation of hot air. Thus, by subjecting a crystalline 2-O-α-D-glucopyranosyl-L-ascorbic acid to conventional chemical reaction under anhydrous conditions, for example, its ether and ester derivatives can be prepared with an ease. These derivatives are favorably usable, for example, in surface active agent, emulsifier, stabilizer and lipophilic vitamin C.

When a crystalline 2-O-α-D-glucopyranosyl-L-ascorbic acid is in free acid form, it can be, if necessary, converted, for example, into sodium salt, calcium salt, magnesium salt, iron salt, copper salt and zinc salt by allowing it to react with an aqueous solution of such as metal hydroxide and metal carbonate, so that the resultant substance is imparted with abilities of adequately adjusting pH and also exhibiting the activities of minerals and vitamin C. Such a substance is favorably usable in nutritive fortifiers and chemical agents.

The following experiments will explain in detail a typical crystalline 2-O-α-D-glucopyranosyl-L-ascorbic acid according to the invention.

Experiment 1

Preparation of Crystalline
2-O-α-D-glucopyranosyl-L-ascorbic acid

Nine parts by weight of dextrin (DE about 6) was dissolved in 15 parts by weight of water by heating, and the solution was added with 3 parts by weight of L-ascorbic acid under reducing conditions, further added with 400 units/g dextrin of cyclomaltodextrin glucanotransferase commercialized by Hayashibara Biochemical Laboratories, Inc., Okayama, Japan, and allowed to react for 24 hours while keeping the solution at pH 5.5 and 60° C. The reaction mixture was fed to "AQ-303 ODS" HPLC system, a product of Yamamura Chemical Laboratories Co., Ltd., Kyoto, Japan, equipped with "LC-6" column, a product of Shimadzu Seisakusho Ltd., Kyoto, Japan, and eluted with 0.1M $KH_2PO_4$—$H_3PO_4$ buffer (pH 2.0) at a flow rate of 0.5 ml/minute while monitoring with "MULT-340" detector system, a product of Japan Spectroscopic Co., Ltd., Tokyo, Japan. As the result, L-ascorbic acid appeared at a retension time of 9.5 minutes, while the newly formed α-D-glucosyl-L-ascorbic acid, maltosyl-L-ascorbic acid, α-D-maltotriosyl-L-ascorbic acid, α-D-maltotetraosyl-L-ascorbic acid, α-D-maltopentaosyl-L-ascorbic acid, α-D-maltohexaosyl-L-ascorbic acid and α-D-maltoheptaosyl-L-ascorbic acid appeared at respective retension time of 11.2 minutes, 15.7 minutes, 20.6 minutes, 24.9 minutes, 28.1 minutes, 32.1 minutes and 38.6 minutes. About 60% of the L-ascorbic acid was converted into α-glycosyl-L-ascorbic acid. Thereafter, the reaction mixture was filtered with UF membrane to remove the enzyme, adjusted to pH 5.0 and 55° C., added with 10 units/g dextrin of glucoamylase (EC 3.2.1.3) commercialized by Seikagaku Kogyo Ltd., Tokyo, Japan, and allowed to react for 24 hours. HPLC analysis of the reaction mixture revealed that α-D-maltosyl-L-ascorbic acid and higher α-glycosyl-L-ascorbic acids were hydrolyzed into 2-O-α-D-glucopyranosyl-L-ascorbic acid.

The reaction mixture was then heated to inactive the remaining enzyme, decolored and filtered with activated carbon, and the filtrate was concentrated to about 50 w/w %.

The concentrate was subjected to column chromatographed on "XT-1016 (Na⁺-form)", a strongly-acidic cation exchange resin commercialized by Tokyo Chemical Industries, Tokyo, Japan, in accordance with the method disclosed in Japanese Patent Laid-Open No.23,799/83 with a slight modification to elute and recover a 2-O-α-D-glucopyranosyl-L-ascorbic acid-rich fraction, purity of about 94%, which was then purified by the demineralization using a cation exchange resin (H⁺-form), concentrated to about 80 w/w %, placed in a glass vessel, and allowed to stand at 20°–35° C. for about 1 month. Thus, crystallization occurred. A portion of the crystal was added to a fresh preparation of the same purified and concentrated 2-O-α-D-glucopyranosyl-L-ascorbic acid-rich fraction, and crystallized by gentle stirring. The resultant massecuite was separated into the molasses and crystal, and the latter was then washed by spraying thereto a small amount of chilled water for a higher purity, dissolved in water and recrystallized. Thus, a high-purity crystal, purity of about 99.9% or higher, was obtained.

Experiment 2

Physicochemical Properties Of Crystalline 2-O-α-D-glucopyranosyl-L-ascorbic acid Characterization of a crystal, obtained by the recrystallization in accordance with the method in Experiment 1, revealed that it was a novel anhydrous crystalline 2-O-α-D-glucopyranosyl-L-ascorbic acid.

The properties of the crystal will be described hereinafter.

(1) Elemental analysis
  Found; C=42.6%, H=5.36%
  Calculated; C=42.4%, H=5.37%, N<0.01% (for chemical formula $C_{12}H_{18}O_{11}$)

(2) Molecular weight
  FD mass spectrometric analysis with "M-80B", a mass spectrometry commercialized by Hitachi Ltd., Tokyo, Japan, revealed a (M+H)⁺ peak at 339 (molecular weight for chemical formula $C_{12}H_{18}O_{11}$ is 338).

(3) Melting point
  158.5°–159.5° C.

(4) Heat of dissolution
  Endothermic (27.2 kcal/g)

(5) Specific rotation
  $[\alpha]_D^{20}$=+189 6° (H₂O, pH 1.98)
  $[\alpha]_D^{20}$=+246.3° (H₂O, pH 7.10)

Figure 2:
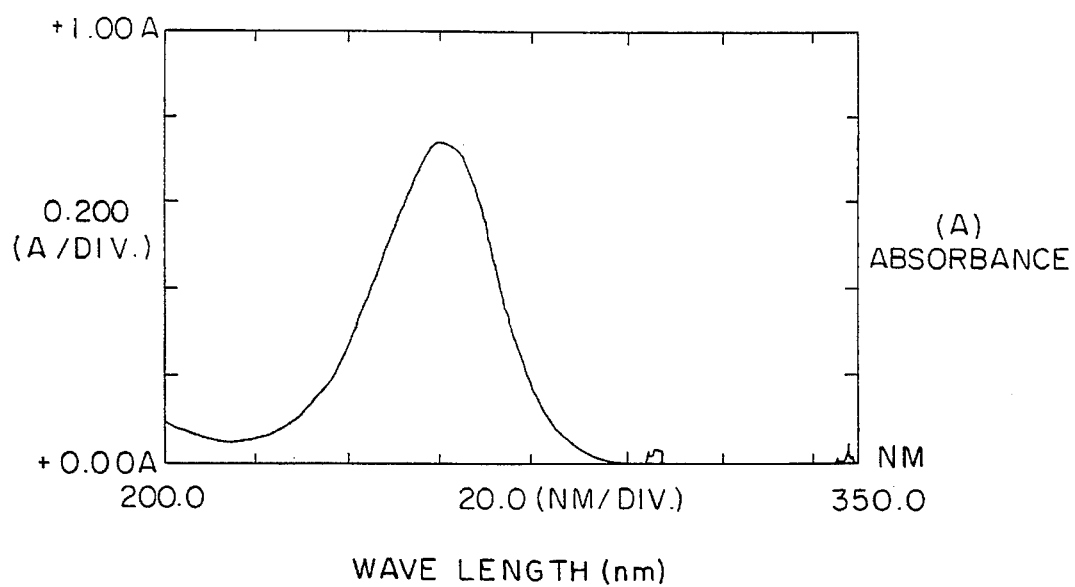
FIG. 2 is the uv-absorption spectrum of the crystalline 2-O-α-D-glucopyranosyl-L-ascorbic acid when in a solution at pH 7.0.

(6) uv-Absorption spectrum
  uv-absorption spectrum was determined in 50 μM solution. The spectrum at pH 2.0 was as shown in FIG. 1, while that at pH 7.0 was as shown in FIG. 2.
  λ(max)=238 nm, ε=0.93×10⁴ (pH 2.0)
  λ(max)=260 nm, ε=1.50×10⁴ (pH 7.0)

Figure 3:
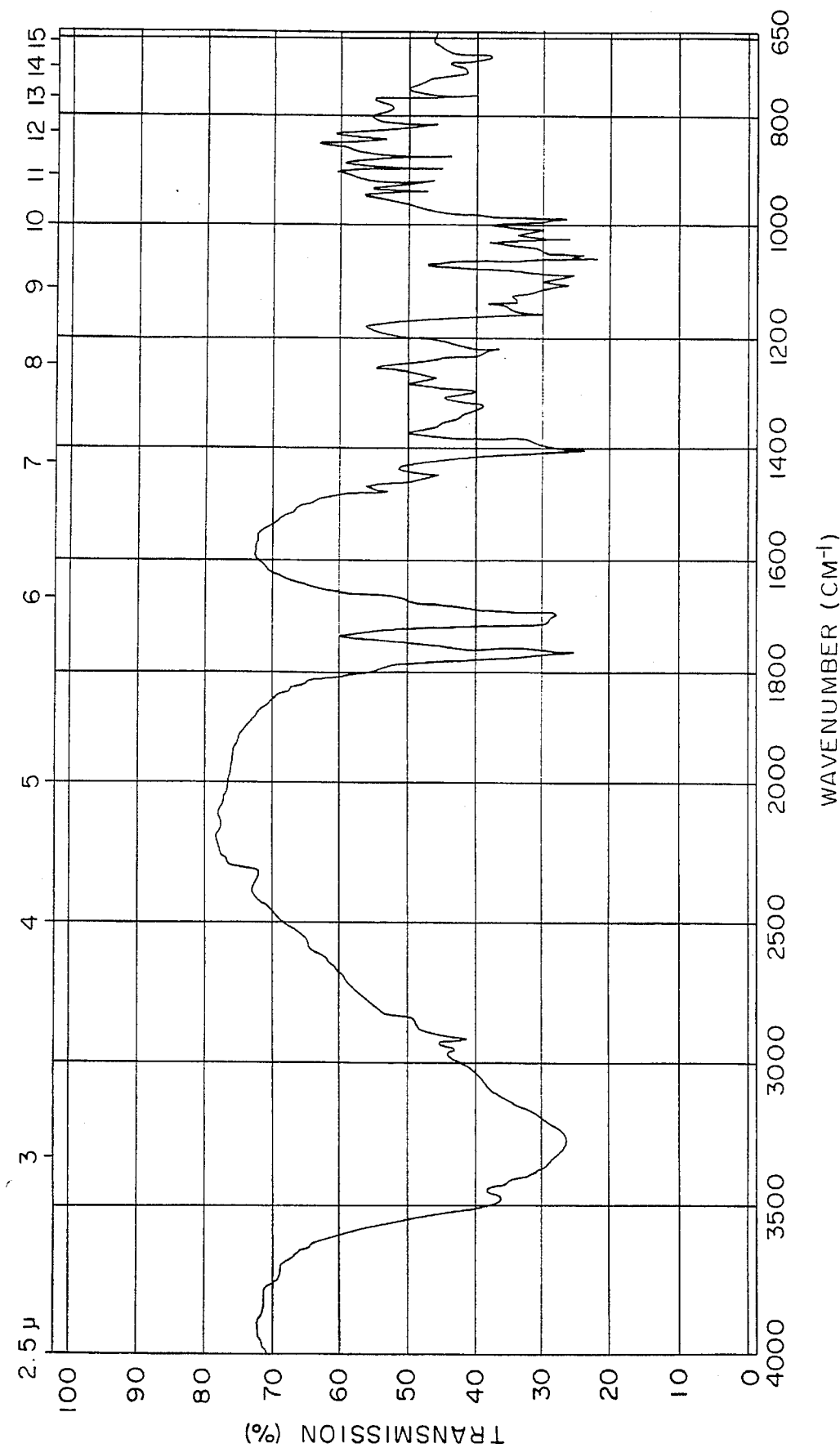
FIG. 3 is the infrared absorption spectrum of the crystalline 2-O-α-D-glucopyranosyl-L-ascorbic acid.
Figure 4:
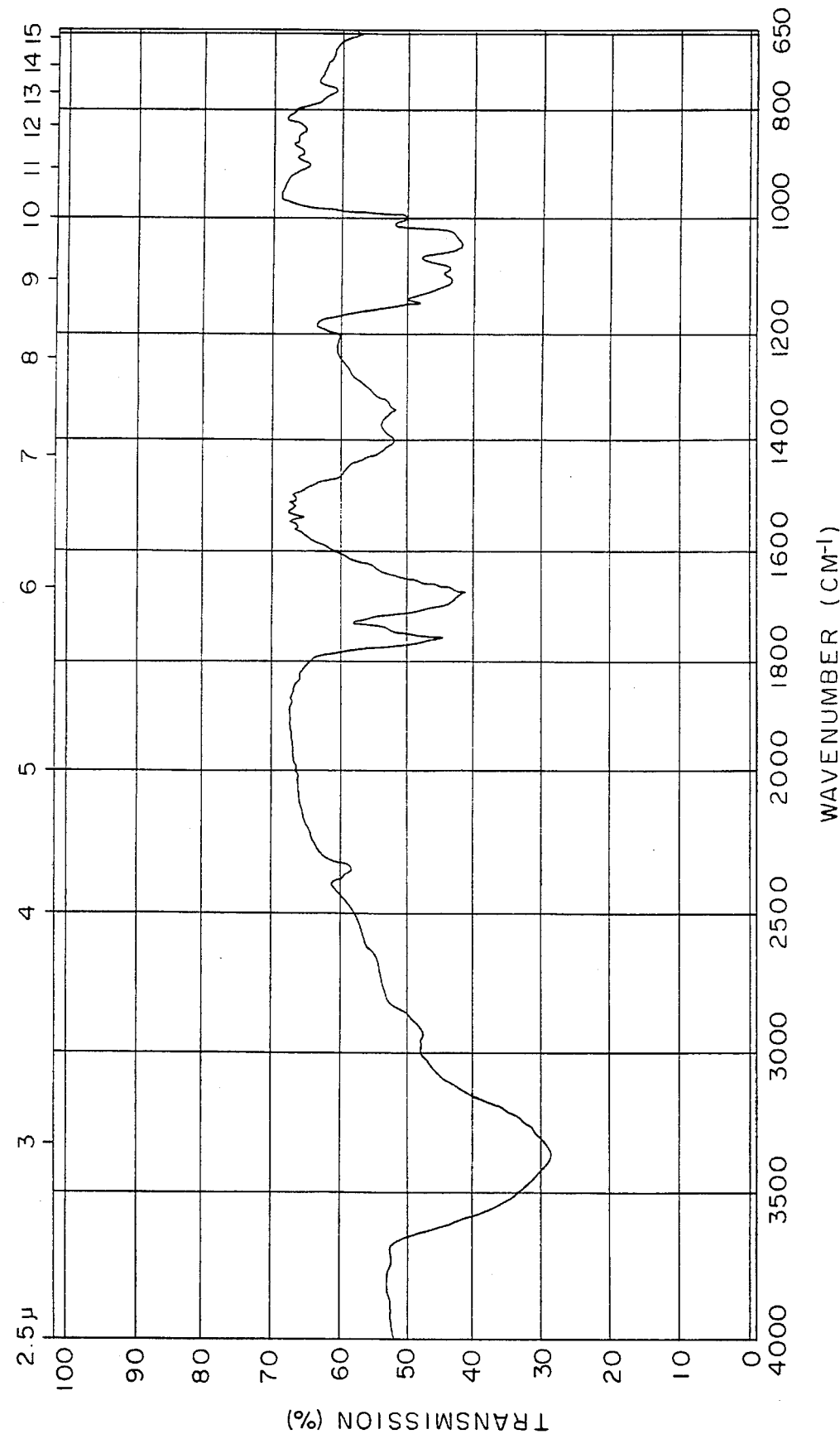
FIG. 4 is the infrared absorption spectrum of an amorphous 2-O-α-D-glucopyranosyl-L-ascorbic acid as the control.

(7) Infrared absorption spectrum
  The KBr tablet method was used. The infrared spectrum of the crystal was as shown in FIG. 3, while that of an amorphous substance as the control was as shown in FIG. 4.

(8) Solubility
  One hundred and twenty-five grams of the crystal dissolves in 100 g water at 25° C.

(9) Solubility in solvents
  Readily soluble in water, 0.1N sodium hydroxide and 0.1N acetic acid; soluble in methanol and ethanol; and insoluble in ether, benzene, chloroform and ethyl acetate.

(10) Dissociation constant
  The pKa is 3.0. Comparison of this to those for various derivatives of L-ascorbic acid in Table 1 in J.Jernow et al., *Tetrahedron*, Vol.35, pp.1,483–1,486 (1979) and in Table 2 in Pao-Wen Lu et al., *Journal of Agricultural Food Chemistry*, Vol.32, pp.21–28 (1984) suggests that in the substance of the invention, the alcohol group which is located at the number two carbon atom in the ascorbic acid moiety is responsible for the α-D-glucosyl linkage, while the alcohol group which is located at the number three carbon atom is in free form.

(11) Methylation analysis
  The crystal was methylated by the method described in Pao-Wen Lu et al., *Journal of Agricultural Food and Chemistry*, Vol.32, pp.21–28 (1984) wherein L-ascorbic acid was methylated with diazomethane to predominantly form 3-O-methyl-L-ascorbic acid. A subsequent hydrolysis of the resultant led to the formation of 3-O-methyl-L-ascorbic acid and D-glucose as the predominant products.

Figure 5:
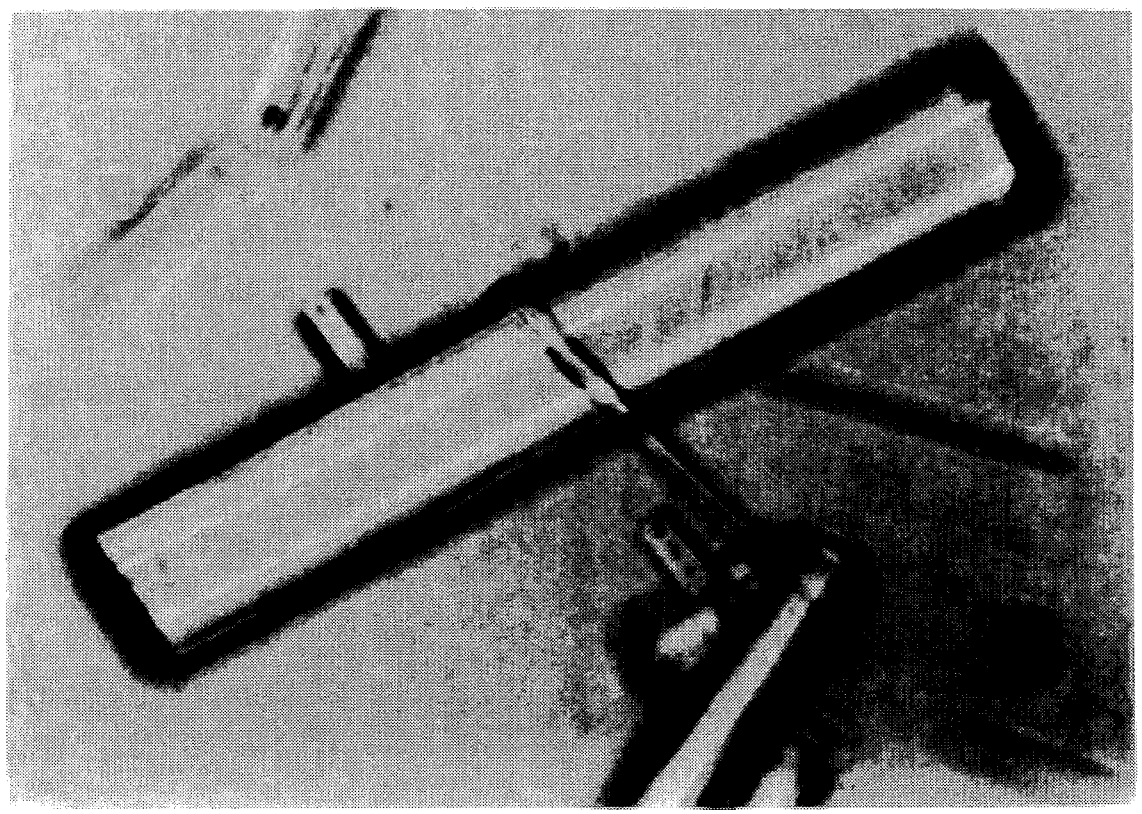
FIG. 5 is the microscopic view of a crystal grown in a supersaturated solution (x40).

(12) Physical properties and color
  Colorless and transparent crystal. When pulverized, the crystal exhibits a sour taste, but exhibits no odor. Free of hygroscopicity and deliquescence. Loss on drying at 130° C. for 2 hours is less than 0.5 w/w %. FIG. 5 is the microscopic view of a crystal growing in a supersaturated solution.

(13) Coloring reaction
  Exhibiting no direct reducing activity, and not reducing and decoloring 2,6-dichlorophenolindophenol.
  Negative to the 2,4-dinitrophenylhydrazine reaction.
  Turning green on the anthrone-sulfuric acid reaction.

(14) Structural element
  Hydrolyzable by α-glucosidase or by treatment with 1N hydrochloric acid at 100° C. for 5 minutes to form L-ascorbic acid and D-glucose at a molar ratio of 1:1.

(15) Powder x-ray diffraction analysis
  On powder x-ray diffraction analysis using "GEIGER-FLEX RAD-II B (CuKα ray)", a product of Rigaku Corp., Tokyo, Japan, the crystal exhibits predominant diffraction angles (2θ) of 10.3°, 14.8°, 16.2°, 18.4° and 24.5°.

Figure 6:
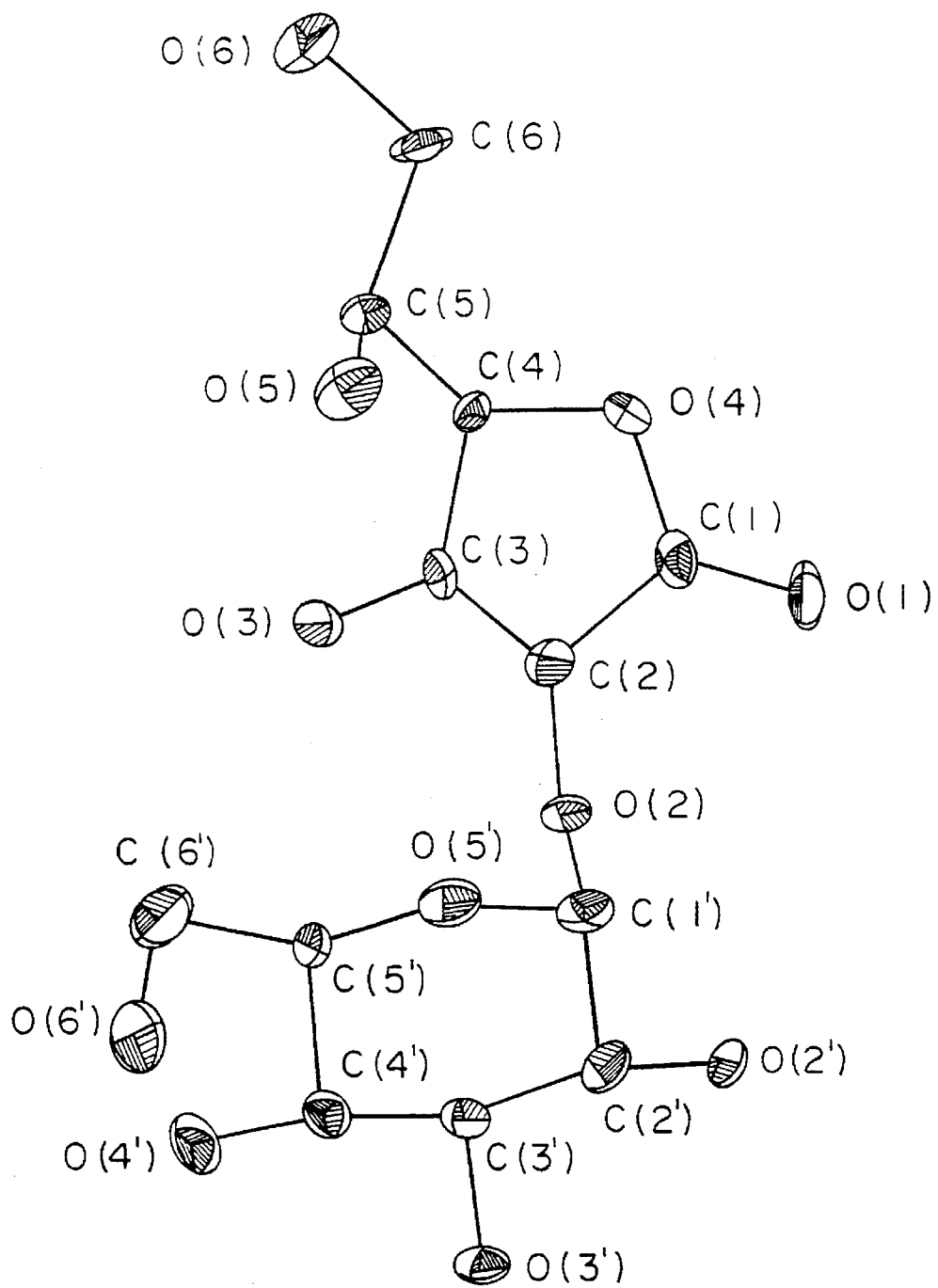
FIG. 6 is the ORTEP figure of a crystalline 2-O-α-D-glucopyranosyl-L-ascorbic acid according to the invention.

(16) x-Ray analysis on single crystal
  x-Ray diffraction analysis on a single crystal grown in a supersaturated solution revealed that it was grouped into the orthorhombic system, and its space group was $P2_12_12_2$ with lattice constants of a=11.929 Å, b=24.351 Å and c=4.864 Å (α=β=γ=90°).
  These data evidently show that in the chemical structure of the crystal, an α-glucosyl linkage is formed between the alcohol group at the number two carbon atom and the alcohol group which is located at the number one carbon atom in D-glucose.
  FIG. 6 is the ORTEP figure of the crystal.

The above data suggest that the crystal is a novel crystalline 2-O-α-D-glucopyranosyl-L-ascorbic acid shown by the formula [III]:

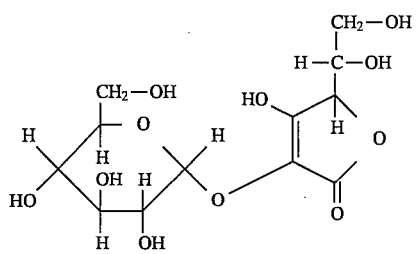

Consequently, it is suggested that α-glycosyl-L-ascorbic acid wherein equimolar or more D-glucose residues are bound to L-ascorbic acid has the chemical structure shown by the formula [IV]:

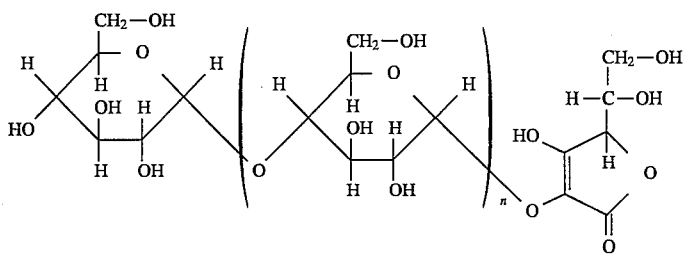

wherein n is an integer from 0 to 6.

Experiment 3

Stability of Crystalline

2-O-α-D-glucopyranosyl-L-ascorbic acid in solution

2-O-α-D-Glucosyl-L-ascorbic acid was compared respectively to the 6-O-α-D-glucosyl-L-ascorbic acid disclosed in Japanese Patent Publication No.38,158/73, and L-ascorbic acid for their stability in aqueous solution. More particularly, each sample was adjusted to a concentration of 70 micromoles and to pH 7.0 or 2.0, placed in a cuvette, and measured for its absorbance at either 260 nm and pH 7.0 or at 245 nm and pH 2.0 while keeping the solution at 45° C. The remaining ratio (%) was calculated with the absorbance.

The results were as shown in Table I.

As obvious from the results in Table I, unlike 6-O-α-D-glucosyl-L-ascorbic acid and L-ascorbic acid, crystalline 2-O-α-D-glucopyranosyl-L-ascorbic acid is extremely stable even in aqueous solution.

TABLE I

| pH | | Time (hour) | | | | | |
|---|---|---|---|---|---|---|---|
| | | 0 | 1 | 2 | 4 | 18 | 24 |
| 7 | 2GAsA | 100% | 100% | 100% | 100% | 100% | 100% |
| | 6GAsA | 100% | 88% | 72% | 43% | 7% | 4% |
| | AsA | 100% | 80% | 61% | 32% | 1% | 1% |
| 2 | 2GAsA | 100% | 100% | 100% | 100% | 100% | 100% |
| | 6GAsA | 100% | 99% | 98% | 90% | 25% | 12% |
| | AsA | 100% | 98% | 95% | 88% | 12% | 4% |

Note: 2GAsA is the symbol for the crystalline 2-O-α-D-glucopyranosyl-L-ascorbic acid of the invention; 6GAsA, for 6-O-α-D-glucosyl-L-ascorbic acid as a control; and AsA, for L-ascorbic acid as another control.

Experiment 4

Acute Toxicity

A crystalline 2-O-α-D-glucopyranosyl-L-ascorbic acid specimen, prepared by the method in Experiment 1, was orally administered to 7 week-old dd mice for acute toxicity test. As the result, no mouse died when administered with up to 5 g of the specimen, and higher dose was difficult.

These confirmed that the specimen was extremely low in toxicity.

The following Examples A and Examples B will illustrate the crystalline 2-O-α-D-glucopyranosyl-L-ascorbic acid and its uses respectively.

EXAMPLE A-1

Crystalline 2-O-α-D-glucopyranosyl-L-ascorbic acid

Nine parts by weight of α-cyclodextrin was dissolved in 20 parts by weight of water by heating, and the solution was added with 3 parts by weight of L-ascorbic acid under reducing conditions, thereafter while keeping the solution at pH 5.5 and 65° C., added with 100 units/g α-cyclodextrin of cyclomaltodextrin glucanotransferase commercialized by Hayashibara Biochemical Laboratories, Inc., Okayama, Japan, and allowed to react for 40 hours. HPLC analysis of the reaction mixture revealed that about 50% of the L-ascorbic acid was converted into α-glycosyl-L-ascorbic acid similarly as in Experiment 1.

Thereafter, the reaction mixture was heated to inactivate the remaining enzyme, adjusted to pH 4.5 and 55° C., added with 50 units/g α-cyclodextrin of glucoamylase, and allowed to react for 24 hours. HPLC analysis of the newly formed reaction mixture revealed that α-maltosyl-L-ascorbic acid and higher α-glycosyl-L-ascorbic acids were hydrolyzed into 2-O-α-D-glucopyranosyl-L-ascorbic acid.

The reaction mixture was then heated to inactivate the remaining enzyme, decolored and filtered with activated carbon, and the filtrate was applied to a column of a cation exchange resin ($H^+$ -form) for demineralization, further applied to a column of an anion exchange resin ($OH^-$-form) to adsorb anions. Thereafter, the column was washed with water and applied with 0.5N hydrochloric acid for elution, and the eluate was subjected to gel filtration chromatography on "HW-40", a gel product of Tosoh Corp., Tokyo, Japan, to recover a 2-O-α-D-glucopyranosyl-L-ascorbic acid-rich fraction which was then concentrated in vacuo to about 73-w/w %, placed in a crystallizer, added with 1 w/w % 2-O-α-D-glucopyranosyl-L-ascorbic acid seed crystal, adjusted to 40° C., gradually cooled to 25° C. over a period of 2 days while accelerating the crystallization by gentle stirring, and fed to a basket-type centrifuge to remove the molasses. The remaining crystal was washed by spraying thereto a small amount of an aqueous ethanol to obtain a crystalline 2-O-α-D-glucopyranosyl-L-ascorbic acid, purity of about 99%, in the yield of about 35 w/w % against the starting L-ascorbic acid.

Although the product was slightly different in such as melting point and specific rotation from a crystal obtained by the method in Experiment 1, the other properties were substantially the same.

The product is substantially nonhygroscopic, easily heandleable, free of direct reducing activity, and satisfactorily high in stability and physiological activities. Thus, the product is favorably usable as a taste-improving agent, souring agent, stabilizer, quality-improving agent, antioxidant, physiologically active agent, uv-absorbent, pharmaceutical material and chemical in foods, beverages, pharmaceuticals for susceptive diseases, cosmetics and chemical reagents, as well as in agents directed to enrich vitamin C.

Experiment A-2

Crystalline 2-O-$\alpha$-D-glucopyranosyl-L-ascorbic acid

Thirty parts by weight of dextrin (DE about 6) was dissolved in 40 parts by weight of water by heating, and the solution was added with 7 parts by weight of L-ascorbic acid under reducing conditions, thereafter while keeping the solution at pH 5.6 and 60° C., added with 250 units/g dextrin of cyclodextrin glucanotransferase and allowed to react for 40 hours. After analyzing the reaction mixture by HPLC similarly as in Example A-1, about 65% of the L-ascorbic acid was converted into $\alpha$-glycosyl-L-ascorbic acid similarly as in Experiment 1.

Thereafter, the reaction mixture was filtered with UF membrane to remove the enzyme, adjusted to pH 5.0 and 50° C., added with 100 units/g dextrin of glucoamylase, and allowed to react for 6 hours. HPLC analysis of the reaction mixture revealed that $\alpha$-D-maltosyl-L-ascorbic acid and higher $\alpha$-glycosyl-L-ascorbic acids were converted into 2-O-$\alpha$-D-glucopyranosyl-L-ascorbic acid.

Thereafter, the reaction mixture was heated to inactivate the remaining enzyme and filtered, after which the filtrate was concentrated and chromatographed on a column of "DOWEX 50WX4 ($Ca^{++}$-form)", a strongly-acidic cation exchange resin commercialized by Dow Chemical Co., Midland, Mich., USA, in accordance with the method in Experiment 1 with a slight modification. The eluted 2-O-$\alpha$-D-glucopyranosyl-L-ascorbic acid-rich fraction was purified by the demineralization with a cation exchange resin ($H^+$-form), concentrated in vacuo to about 77 w/w %, placed in a crystallizer, added with 2 w/w % seed crystal, adjusted to 45° C., and gradually cooled to 28° C. over a period of 2 days while accelerating the crystallization by gentle stirring. The resultant massecuite was separated similarly as in Example 1 to obtain a crystalline 2-O-$\alpha$-D-glucopyranosyl-L-ascorbic acid, purity of about 98%, in the yield of about 45 w/w % against the starting L-ascorbic acid.

Similarly as the product in Example A-I, the product is substantially nonhygroscopic, easily handleable, free of direct reducing activity, and satisfactorily high in stability and physiologial activities. Thus, the product is favorably usable as a taste-improving agent, souring agent, moisture-retaining agent, stabilizer, quality-improving agent, antioxidant, biologically active agent, uv-absorbent, pharmaceutical material and chemical in foods, beverages, pharmaceuticals for susceptive diseases and cosmetics, as well as in agents directed to enrich vitamin C.

EXAMPLE A-3

Crystalline 2-O-$\alpha$-D-glucopyranosyl-L-ascorbic acid

Similarly as in Example A-2, cyclomaltodextrin glucanotransferase and glucoamylase were allowed to react to obtain a reaction mixture containing 2-O-$\alpha$-D-glucopyranosyl-L-ascorbic acid which was then heated to inactivate the enzymes, decolored and filtered with activated carbon. The resultant filtrate was demineralized with a cation exchange resin ($H^+$-form) and chromatographed on a column of a strongly-acidic cation exchange resin ($H^+$-form) in accordance with the method in Experiment 1 with a slight modification, followed by elution. The 2-O-$\alpha$-D-glucopyranosyl-L-ascorbic acid-rich fraction was recovered, concentrated to about 90 w/w %, placed in a crystallizer, added with about 2 w/w % seed crystal, gently stirred for 30 minutes, transferred in a tray, and crystallized and solidified by 3-day standing at 25° C. The content was then removed from the tray, fed to a cutting pulverizer, and dried to obtain a crystalline 2-O-$\alpha$-D-glucopyranosyl-L-ascorbic acid, purity of about 95%, in the yield of about 70 w/w % against the starting L-ascorbic acid.

Similarly as the product in Example A-1, the product is substantially nonhygroscopic, easily handled, free from direct reducing activity, and satisfactorily high in stability and physiological activities. Thus, the product is favorably usable as a taste-improving agent, souring agent, stabilizer, quality-improving agent, antioxidant, physiologically active agent, uv-absorbent, pharmaceutical material and chemical in foods, beverages, pharmaceuticals for susceptive disease, cosmetics and chemical reagents, as well as in agents directed to enrich vitamin C.

EXAMPLE A-4

Crystalline 2-O-$\alpha$-D-glucoyranosyl-L-ascorbic acid

A 2-O-$\alpha$-D-glucopyranosyl-L-ascorbic acid-rich fraction, prepared by the method in Example A-3, was concentrated to about 80 w/w %, placed in a crystallizer, added with about 2 w/w % seed crystal, and gradually cooled from 50° C. while accelerating the crystallization by gentle stirring. The resultant massecuite, crystallinity of about 35%, was sprayed through a nozzle, diameter of 1.5 mm, equipped at the top of a spraying tower with a high-pressure pump, pressure of 150 kg/cm$^2$.

Simultaneously, 85° C. air was passed from the top of the tower towards a net conveyer, provided at the bottom of the tower, to collect the pulverized product on the net conveyer and also to gradually carry the resultant crystalline powder out of the tower over a period of about 30 minutes while passing a stream of 40° C. air upwards through the net.

The crystalline powder was then placed in an ageing tower and aged for 10 hours for crystallization and dehydration. Thus, a crystalline 2-O-$\alpha$-D-glucopyranosyl-L-ascorbic acid, purity of about 95%, was obtained in the yield of about 70 w/w % against the starting L-ascorbic acid.

Similarly as the product in Example A-1, the product is substantially nonhygroscopic, easily handleable, free of direct reducing activity, and satisfactorily high in stability and physiological activities. Thus, the product is favorably usable as a taste-improving agent, souring agent, stabilizer, quality-improving agent, antioxidant, physiologically active agent, uv-absorbent, pharmaceutical material and chemical in foods, beverages, pharmaceuticals for susceptive diseases and cosmetics, as well as in agents directed to enrich vitamin C.

EXAMPLE A-5

Crystalline 2-O-$\alpha$-D-glucopyranosyl-L-ascorbic acid

EXAMPLE A-5(1)

Preparation of $\alpha$-glucosidase

*Mucor javanicus* IFO 4570 was inoculated and cultivated at 30° C. for 44 hours under aeration-agitation conditions in 500 parts by weight of a liquid culture medium which contained water together with 4.0 w/v % maltose, 0.1 w/v % potassium phosphate monobasic, 0.1 w/v % ammonium nitrate, 0.05 w/v % magnesium sulfate, 0.05 w/v % potassium chloride, 0.2 w/v % polypeptone and 1 w/v % calcium carbonate which had been sterilized by heating and sterilely added to the water immediately before the inoculation. After completion of the culture, the mycelia was recovered and immobilized in usual manner.

EXAMPLE A-5(2)

Preparation of Crystalline 2-O-α-D-glucopyranosyl-L-ascorbic acid

Forty parts by weight of "SUNMALT®" a crystalline maltose commercialized by Hayashibara Co., Ltd., Okayama, Japan, was dissolved in 70 parts by weight of water by heating, and the solution was added with 10 parts by weight of L-ascorbic acid under reducing conditions, further added with 10 units/g maltose of an immobilized α-glucosidase prepared by the method in Example A-5(1), and allowed to react at pH 5.5 and 50° C. for 3 hours under light-shielding conditions.

One unit of α-glucosidase is defined as the amount of enzyme that releases 1 micromole glucose at 37° C. over a time period of 1 minute when assayed under the following conditions. After appropriately diluting, 100 microliters of an enzyme solution is added to a mixture solution of 250 microliters of 4 w/v % maltose and 750 microliters of 0.1M acetate buffer (pH 6.0) containing 1.35 mM EDTA, and the mixture is allowed to react at 37° C. for 30 minutes, incubated in boiling water for 3 minutes to suspend the reaction, and centrifuged. Thereafter, 20 microliters of the supernatant is sampled, added with 1 ml of "GLUCOSE B TEST", a coloring reagent for the glucose oxidase method commercialized by Wako Pure Chemical Industries, Ltd., Osaka, Japan, incubated at 37° C. for 20 minutes for color development, and assayed for absorbance at 505 nm.

Thereafter, the reaction mixture was filtered to recover the immobilzied α-glucosidase which was reused in another reaction batch. The filtrate was decolored with activated carbon, and chromatographed on a column of a strongly-acidic cation exchange resin by the method in Example A-2 to recover a 2-O-α-D-glucopyranosyl-L-ascorbic acid-rich fraction which was then purified with a cation exchange resin, thereafter in accordance with the method in Example A-3, concentrated in vacuo to about 90 w/w %, placed in a crystallizer, added with a seed crystal, crystallized and solidified in a tray, fed to a cutting pulverizer, and dried to obtain a crystalline 2-O-α-D-glucopyranosyl-L-ascorbic acid, purity of about 88%, in the yield of about 20 w/w % against the starting L-ascorbic acid.

Comparing to the product in Example A-1, the product is slightly inferior, but substantially nonhygroscopic, easily handleable, free of direct reducing activity, and satisfactorily high in stability and physiological activities. Thus, the product is favorably usable as a taste-improving agent, souring agent, stabilizer, quality-improving agent, antioxidant, physiologically active agent, uv-absorbent, pharmaceutical material and chemical in foods, beverages, pharmaceuticals for susceptive diseases and cosmetics, as well as in agents directed to enrich vitamin C.

EXAMPLE B-1

Chewing Gum

Twenty-five parts by weight of gum base and 20 parts by weight of a crystalline 2-O-α-D-glucopyranosyl-L-ascorbic acid obtained by the method in Example A-2 were kneaded at 60° C. with a mixer, and the mixture was added with 50 parts by weight of "MABIT®", an anhydrous crystalline maltitol commercialized by Hayashibara Shoji Inc., Okayama, Japan, 1.5 parts by weight of calcium phosphate and 0.1 part by weight of an L-menthol including β-cyclodextrin, and further mixed with a small amount of seasoning, rolled and cut to obtain the captioned product. The product is a vitamin C-enriched, low-cariogenic and low-caloric chewing gum.

EXAMPLE B-2

"Gyuhi (starch paste)"

One part by weight of waxy rice starch was mixed with 1.2 parts by weight of water, and the mixture was mixed to homogeneity with 1.5 parts by weight of sucrose, 0.7 parts by weight of "SUNMALT®", a crystalline β-maltose commercialized by Hayashibara Co., Ltd., Okayama, Japan, 0.1 part by weight of a crystalline 2-O-α-D-glucopyranosyl-L-ascorbic acid obtained by the method in Example A-5 while gelatinizing by heating. Thereafter, the resultant was molded and packaged in usual manner to obtain "gyuhi".

The product is a vitamin C-enriched, Japanese-style confectionery with excellent flavor and biting properties, which looks like "kibi-dango (millet dumpling)". The product exhibits a long shelf life because its retrogradation is effectively suppressed.

EXAMPLE B-3

Mixed Sweetener

A mixed sweetener was obtained by mixing 100 parts by weight of honey, 50 parts by weight of isomerized sugar, 2 parts by weight of "kurozato (unrefined sugar)" and 1 part by weight of a crystalline 2-O-α-D-glucopyranosyl-L-ascorbic acid obtained by the method in Example A-3.

The product is a vitamin C-enriched sweetener, and suitable for health food.

EXAMPLE B-4

Chocolate

Forty parts by weight of cacao paste, 10 parts by weight of cacao butter, 50 parts by weight of anhydrous crystalline maltitol and 1 part by weight of a crystalline 2-O-α-D-glucopyranosyl-L-ascorbic acid obtained by the method in Example A-2 were mixed to homogeneity, and the mixture was fed to a refiner to reduce the particle size, transferred to a conche, and kneaded therein at 50° C. for 2 days. In the kneading step, 0.5 parts by weight of tecithin was added and dispersed to homogeneity. Thereafter, the content was adjusted to 31° C. with a thermoregulator, and placed in a mold immediately before the solidification of the butter, deaerated with a vibrator, and solidified by passing it through a 10° C. cooling tunnel over a period of 20 minutes. The content was removed from the mold, and packaged to obtain the captioned product.

The product is free of hygroscopicity and excellent in color, gloss and texture, as well as smoothly melting in the mouth to exhibit a moderate and mild sweetness and flavor. The product is a vitamin C-enriched, low-cariogenic and low-caloric chocolate.

EXAMPLE B-5

Cream Filling

A cream filling was obtained by mixing in usual manner 1,200 parts by weight of "FINETOSE®", a crystalline α-maltose commercialized by Hayashibara Co., Ltd., Okayama, Japan, 1,000 parts by weight of shortening, 10 parts by weight of a crystalline 2-O-α-D-glucopyranosyl-L-ascorbic acid obtained by the method in Example A-4, 1 part by weight of lecithin, 1 part by weight of lemon oil and 1 part by weight of vanilla oil to homogeneity.

The product is a vitamin C-enriched cream filling which is excellent in taste, flavor, melting and biting properties.

EXAMPLE B-6

Tablet

Twenty parts by weight of a crystalline 2-O-α-D-glucopyranosyl-L-ascorbic acid obtained by the method in Example A-1 was mixed to homogeneity with 13 parts by weight of crystalline β-maltose, 4 parts by weight of cornstarch, 1 part by weight of rutin and 0.5 parts by weight of riboflavin, and the resultant was tableted to obtain the captioned product, 150 mg each.

The product is a stable and easily swallowable vitamin compound of vitamin C, vitamin P and vitamin $B_2$.

EXAMPLE B-7

Capsule

Ten parts by weight of calcium acetate monohydrate, 50 parts by weight of magnesium L-lactate trihydrate, 57 parts by weight of maltose, 20 parts by weight of a crystalline 2-O-α-D-glucopyranosyl-L-ascorbic acid obtained by the method in Example A-2, and 12 parts by weight of a γ-cyclodextrin inclusion compound containing 20% eicosapentaenoic acid were mixed to homogeneity, and the mixture was fed to a granulator, and then encapsulated in gelatine to obtain capsules, 150 mg each.

The product is favorably usable as a high-quality blood cholesterol lowering agent, immunopotentiator and skin-refining agent in preventive and remedy for susceptive diseases, as well as in foodstuffs directed to the maintenance and promotion of health.

EXAMPLE B-8

Ointment

One part by weight of sodium acetate trihydrate, 4 parts by weight of DL-calcium lactate and 10 parts by weight of glycerine were mixed to homogeneity, and the mixture was added to another mixture of 50 parts by weight of vaseline, 10 parts by weight of vegetable wax, 10 parts by weight of lanolin, 14.5 parts by weight of sesame oil, 1 part by weight of a crystalline 2-O-α-D-glucopyranosyl-L-ascorbic acid obtained by the method in Example A-5 and 0.5 parts by weight of peppermint oil, and mixed to homogeneity to obtain an ointment.

The product is favorably usable as a high-quality sunscreen agent, skin-refining agent, skin-whitening agent and promoter for healing injury and burn.

EXAMPLE B-9

Injection

A crystalline 2-O-α-D-glucopyranosyl-L-ascorbic acid, obtained by the recrystallization in accordance with the method in Experiment 1, was dissolved in water, neutralized and sterilely filtered in usual manner to obtain a pyrogen-free solution which was then distributed to 20 ml glass vials to give a 2-O-α-D-glucopyranosyl-L-ascorbic acid content of 500 mg, dried in vacuo and sealed to obtain the captioned product.

The product is intramuscularly and intravenously administrable alone or in combination with vitamins and minerals. The product requires no cold storage, and exhibits an excellently high solubility in saline when in use.

Besides supplementing vitamin C, the product acts as an antioxidant to exert both activated oxygen-removing and lipoperoxide formation-inhibiting effects when hydrolyzed. Thus, the product is favorably usable in preventive and remedy for various susceptive diseases such as viral diseases, bacterial diseases, traumatic diseases, rheumatism, immunopathies, allergy, diabetes, cataract, circulatory diseases and malignant tumors.

EXAMPLE B-10

Injection

Six parts by weight of sodium chloride, 0.3 parts by weight of potassium chloride, 0.2 parts by weight of calcium chloride, 3.1 parts by weight of sodium lactate, 48 parts by weight of maltose and 2 parts by weight of a crystalline 2-O-α-D-glucopyranosyl-L-ascorbic acid obtained by the method in Example A-1 were dissolved in 1,000 parts by weight of water, and sterilely filtered in usual manner, and 250 ml aliquots of the resultant pyrogen-free solution were distributed to sterilized plastic vessels to obtain the captioned product.

The product is usable in the supplement of vitamin C, calorie and minerals. The product acts as an antioxidant to exert both activated oxygen-removing and lipoperoxide formation-inhibiting effects when hydrolyzed. Thus, the product is favorably usable in the restoration of health during and before suffering from diseases, as well as in preventive and remedy for susceptive diseases such as viral diseases, bacterial diseases, traumatic diseases, rheumatism, immunopathies, allergy, diabetes, cataract, circulatory diseases and malignant tumors.

EXAMPLE B-11

Intubation Nutrient

Twenty four gram aliquots of a compound consisting of 20 parts by weight of crystalline α-maltose, 1.1 parts by weight of glycine, 0.18 parts by weight of sodium glutamate, 1.2 parts by weight of sodium chloride, 1 part by weight of citric acid, 0.4 parts by weight of calcium lactate, 0.1 part by weight of magnesium carbonate, 0.1 part by weight of a crystalline 2-O-α-D-glucopyranosyl-L-ascorbic acid obtained by the method in Example A-3, 0.01 part by weight of thyamine and 0.01 part by weight of riboflavin were packed in laminated aluminum bags, and heat-sealed to obtain the captioned product.

In use, one bag of the product is dissolved in about 300–500ml of water, and the solution is favorably usable as an intubation nutrient directed to oral and parenteral administration to the nasal cavity, stomach and intestine.

EXAMPLE B-12

Bath Liquid

A bath liquid was obtained by mixing 21 parts of DL-sodium lactate, 8 parts by weight of sodium pyruvate, 5 parts by weight of a crystalline 2-O-α-D-glucopyranosyl-L-ascorbic acid powder obtained by the method in Example A-5 and 40 parts by weight of ethanol with 26 parts by eight of refined water and appropriate amounts of coloring agent and flavoring agent.

The product is suitable for skin-refining agent and skin-whitening agent, which is diluted by 100–10,000-folds in bath water when in use. In this case, bath water is replaceable with cleansing liquid, astringent and moisture liquid.

EXAMPLE B-13

Milky Lotion

One half part by weight of polyoxyethylene behenyl ether, 1 part by weight of polyoxyethylene sorbitol tetraoleate, 1 part by weight of oil-soluble glyceryl monostearate, 0.5 parts by weight of pyruvic acid, 0.5 parts by weight of behenyl alcohol, 1 part by weight of avocado oil, 1 part by weight of a crystalline 2-O-α-D-glucopyranosyl-L-ascorbic acid obtained by the method in Example A-4 and appropriate amounts of vitamin E and antiseptic were dissolved in usual manner by heating, and the solution was added with 1 part by weight of L-sodium lactate, 5 parts by weight of 1,3-butylene glycol, 0.1 part by weight of carboxyvinyl polymer and 85.3 parts by weight of refined water, emulsified with a homogenizer, added with an appropriate amount of flavoring agent, and mixed by stirring to obtained the captioned product.

The product is favorably usable as a high-quality sun-screen agent, skin-refining agent and skin-whitening agent.

EXAMPLE B-14

Cosmetic Cream

Two parts by weight of polyoxyethylene glycol monostearate, 5 parts by weight of self-emulsifying glycerine monostearate, 2 parts by weight of a crystalline 2-O-α-D-glucopyranosyl-L-ascorbic acid obtained by the method in Example A-3, 1 part by weight of liquid paraffin, 10 parts by weight of glyceryl trioctanate and an appropriate amount of antiseptic were dissolved in usual manner by heating, and the mixture was added with 2 parts by weight of L-lactic acid, 5 parts by weight of 1,3-butylene glycol and 66 parts by weight of refined water, emulsified with a homogenizer, added with an appropriate amount of flavoring agent, and mixed by stirring to obtained the captioned product.

The product is favorably usable as a high-quality sun-screen cream, skin-refining agent and skin-whitening agent.

As described above, crystalline 2-O-α-D-glucopyranosyl-L-ascorbic acid, a novel substance of the invention, is substantially nonhygroscopic, free of deliquescence, consolidation and direct reducing activity, easily handleable, superiorly stable, and readily hydrolyzable in vivo to exhibit the antioxidant and physiological activities inherent to L-ascorbic acid. Furthermore, 2-O-α-D-glucopyranosyl-L-ascorbic acid is a highly safe substance because it is synthesized and metabolized in vivo.

Crystalline 2-O-α-D-glucopyranosyl-L-ascorbic acid is easily crystallizable in a supersaturated solution which is obtainable by allowing a saccharide-transferring enzyme to act alone or together with glucoamylase on a solution containing L-ascorbic acid and an α-glucosyl saccharide, and purifying and concentrating the resultant 2-O-α-D-glucopyranosyl-L-ascorbic acid. Thus, such a crystallization process is superior in economical efficiency, and commercializable with an ease.

Since crystalline 2-O-α-D-glucopyranosyl-L-ascorbic acid is satisfactorily high in stability and physiological activities, it is favorably usable as a stabilizer, quality-improving agent, antioxidant, physiologically active agent, uv-absorbent pharmaceutical material and chemical in foodstuffs including beverages and processed foods, preventive and remedies for susceptive diseases, and cosmetics including skin-refining agent and skin-whitening agent. Thus, crystalline 2-O-α-D-glucopyranosyl-L-ascorbic acid has an extensive use, and is very significant in these industries.

We claim:

1. A crystalline 2-O-α-D-glucopyranosyl-L-ascorbic acid.

2. The crystalline 2-O-α-D-glucopyranosyl-L-ascorbic acid of claim 1, which exhibits predominant diffraction angles (2θ) of 10.3°, 14.8°, 16.2°, 18.4° and 24.5° on powder x-ray diffraction analysis.

\* \* \* \* \*